United States Patent [19]

Lin et al.

[11] Patent Number: 5,780,697
[45] Date of Patent: Jul. 14, 1998

[54] TRIALKYL ALUMINUM DISPLACEMENT PROCESS

[75] Inventors: Ronny Wen-Long Lin; Richard Andrew Holub, both of Baton Rouge, La.; Richard Neil Hollenshead, Houston, Tex.

[73] Assignee: Amoco Corporation, Chicago, Ill.

[21] Appl. No.: 877,756

[22] Filed: Jun. 17, 1997

[51] Int. Cl.$^6$ .................... C07C 2/88; C07C 6/00
[52] U.S. Cl. .............. 585/328; 585/522; 585/637; 556/187; 556/190
[58] Field of Search ..................... 585/328, 637, 585/522; 556/187, 190

[56] References Cited

U.S. PATENT DOCUMENTS 4,918,254   4/1990   Diefenbach et al. ............... 585/328

*Primary Examiner*—Bekir L. Yildirim
*Attorney, Agent, or Firm*—Joseph DiSalvo; Stephen L. Hensley

[57] ABSTRACT

A process for deactivating a nickel, cobalt, or nickel and cobalt displacement catalyst during a reaction wherein an alkyl group is displaced from a trialkyl aluminum compound in a reaction mixture containing said catalyst is disclosed. The process involves adding a deactivating amount of a catalyst poison containing silver, silver compounds, silver complexes, thallium, thallium compounds, thallium complexes, or mixtures thereof to the reaction mixture after the displacement has proceeded to the desired extent.

17 Claims, No Drawings

TRIALKYL ALUMINUM DISPLACEMENT PROCESS

FIELD OF THE INVENTION

The invention, in a broad sense, relates to methods for production of 1-olefins by the well known process of carbon number chain growth of aluminum alkyls. More specifically, it concerns the portion of the process wherein the desired 1-olefins are displaced from the aluminum alkyls in the presence of a displacement/isomerization catalyst. It is also related to isomerization of internal olefins to 1-olefins and to the formation of more desired trialkyl aluminum compounds, both of which are frequently part of the process for production of 1-olefins It is a common practice in such processes to deactivate (kill or poison) the catalyst at a predetermined appropriate time when the optimum mix of desired product will be available. This invention involves the use of silver, silver compounds, thallium, thallium compounds, and mixtures thereof as catalyst killer in these processes.

BACKGROUND OF THE INVENTION

The displacement of an alkyl group or alkyl groups from a trialkyl aluminum compound in the presence of a nickel or cobalt catalyst is a well-studied reaction procedure. The procedure is an integral part of many processes for the formation of aluminum alkyls, processes involving chain growth/displacement, and so-called double displacement processes. One mechanism for the displacement, particularly in the case of nickel, has been discussed in *Angewandte Chemie* by K. Fisher et. al., Volume 12, No. 12, pages 943–953 (December 1973). According to Fisher, the trialkyl aluminum is believed to reduce the nickel supplied to nickel metal, the nickel metal in turn reacting with n-olefin to form an olefin complex. The olefin complex is then believed to react with trialkyl aluminum to displace the alkyl groups bonded to aluminum in an equilibrium reaction.

A problem with nickel and cobalt catalysts in displacement processes is that their presence in the reaction mixture also causes undesirable side reactions. These side reactions include reverse displacement, isomerization of the alpha olefin to internal olefin, dimerization, and branch chain formation isomerization. These side reactions as above were discussed to some extent by Poe et al., Symposium on Production and Use of Alpha Olefins, Div. of Petrol. Chem., Am. Chem. Soc., Los Angeles, Mar. 31–Apr. 5, 1963.

U.S. Pat. No. 4,918,254 (Diefenbach et al.), incorporated herein by reference, discloses a process for the displacement of alkyl groups from a trialkyl aluminum or mixture of trialkyl aluminum compounds in which the undesired side reactions are prevented or inhibited. According to the patentees, a catalyst "poison", i.e., a material which deactivates the catalyst or at least inhibits the unwanted side reactions, is added to the reaction mixture at an appropriate time, in an amount sufficient to prevent the unwanted side reactions. Lead or copper, suitably supplied in solution, or in finely-divided form, is used as the "poison" to interrupt the displacement reaction process.

For a variety of reasons, efforts have recently been directed toward limiting the amounts of lead employed in reaction processes. One reason, with respect particularly to displacement reaction mixtures, relates to the forms in which lead is used and in which it must be recovered. More particularly, the most efficient lead catalyst poison is a solution containing $Pb^{++}$ ion. In the displacement reaction system, part of the $Pb^{++}$ added is reduced in the "poisoning" process to elemental lead, the latter being readily removed. Unfortunately, a further portion of the $Pb^{++}$ added reacts with alkenyl moieties in the solution to form Pb alkyl, a relatively thermally stable composition. The Pb alkyl remains in the process stream at residual levels and possibly could end up in the process mixture to the extent of parts per million or even greater concentrations. For many applications, the presence of Pb at these levels in the process mixture is unacceptable. Accordingly, there has existed a need for a suitable "poison" for nickel and/or cobalt catalysts in displacement reaction process mixtures which does not contain lead. The invention addresses this need.

SUMMARY OF THE INVENTION

In its broadest sense, therefore, the invention relates to a novel process for deactivating a catalyst selected from nickel, cobalt, or mixtures thereof, present in a reaction mixture wherein an alkyl group is displaced from a trialkyl aluminum and in which the displacing action results in the formation of a 1-olefin from the displaced alkyl group. According to the invention, there is added to the reaction mixture, after the displacement reaction has proceeded to the desired extent, instead of lead or copper, a catalyst poison or deactivator comprising or containing silver, thallium, or a mixture of silver and thallium. The silver and/or thallium catalyst poison may be supplied in any suitable form, e.g., as the metal, a mixture of the metals, a deactivating compound or complex of the metals, mixtures thereof, and mixtures of the metal or metals and deactivating compound, compounds, complex, or complexes thereof, as a solid or solids, or in solution. The catalyst poison containing silver and/or thallium will be supplied in an amount sufficient to deactivate the displacement catalyst.

In a more specific aspect, the invention relates to a process for the displacement of an alkyl group or groups from a first trialkyl aluminum compound, or mixture thereof, to form a second trialkyl aluminum compound or mixture thereof comprising, contacting the first trialkyl aluminum compound, or mixture thereof, with a 1-olefin, or mixture of 1-olefins containing a different distribution of carbon atoms than the alkyl groups in the first trialkyl aluminum compound or mixture thereof, in the presence of a nickel, cobalt, or mixture of nickel and cobalt, catalyst under displacement conditions. The 1-olefin or 1-olefins displace at least some of the alkyl groups in the first trialkyl aluminum compound, or mixture thereof, to form a second trialkyl aluminum compound, or mixture thereof. According to the invention, to prevent undesired side reactions, a deactivating amount of a silver, thallium, or mixture of silver and thallium, catalyst poison, as described, supra, is added to the reaction mixture after the reaction has proceeded to the desired extent, preferably before any significant isomerization of the 1-olefins derived from the displaced alkyl group or groups to internal olefins has occurred.

In a further embodiment, the invention relates to a process for preparing an alkylaluminum compound or compounds from an internal olefin or olefins comprising contacting an internal olefin, preferably containing from 4 to 30 carbon atoms, or mixtures thereof, under isomerization and displacement conditions with a catalyst comprising nickel, cobalt, or mixtures of nickel and cobalt to isomerize the internal olefinic bond to form 1-olefin or 1-olefins, in a reaction zone containing a trialkyl aluminum compound or compounds. 1-olefin or 1-olefins formed displacing alkyl groups from the trialkyl aluminum compound or compounds, forming a trialkyl aluminum compound or compounds wherein at least one of the alkyl groups bound to the aluminum is an alkyl group derived from the 1-olefin or olefins, and a silver and/or thallium catalyst poison, as described, supra, is added to the reaction mixture after the reaction has proceeded to the desired extent.

In yet another embodiment, the invention relates to a process wherein an internal olefin, or mixture thereof, preferably comprising an internal olefin containing from 4 to 30 carbon atoms, is contacted with a catalyst comprising nickel, cobalt, or mixtures of cobalt and nickel to isomerize the internal olefinic bond to form 1-olefin or 1-olefins in a reaction zone containing a trialkyl aluminum compound or compounds under isomerization and displacement conditions, with 1-olefin or 1-olefins formed displacing alkyl groups from the trialkyl aluminum compound or compounds, forming a 1-olefin or 1-olefins and an alkyl aluminum compound or compounds wherein at least one of the alkyl groups bound to the aluminum is an alkyl group derived from the 1-olefin or 1-olefins, the catalyst is deactivated by the addition of a catalyst poison after the reaction has proceeded to the desired extent, as described herein, and the 1-olefin or 1-olefins formed by the displaced alkyl group or groups, and the reaction mixture, are removed from the reaction zone.

In yet a further embodiment, ethylene is supplied under suitable conditions to a reaction zone containing a trialkyl aluminum compound or compounds and a nickel, cobalt, or nickel and cobalt catalyst, the ethylene producing, by chain growth mechanism, an alkyl group or groups of greater length in the trialkyl aluminum compound or compounds. The alkyl group or groups of greater length are then displaced by a 1-olefin or 1-olefins to form a 1-olefin of increased length, and a silver, thallium, or silver and thallium catalyst poison according to the invention is supplied to the reaction mixture to deactivate the catalyst after the reaction has proceeded to the desired extent.

DETAILED DESCRIPTION OF THE INVENTION

As will be recognized by those of ordinary skill in the art, the invention has general applicability to displacement processes in which one or more 1-olefins are removed from a trialkyl aluminum compound or compounds, including trialkyl aluminum compounds containing different alkyl groups in a single molecule (asymmetric), and mixtures of different trialkyl aluminum compounds, with the 1-olefin or 1-olefins displaced or removed preferably containing from 3 through 30 or more carbon atoms. Compositions to which the invention is applicable include tri-n-propyl aluminum; tri-n-butyl aluminum; tri-isobutyl aluminum; tri-n-hexyl aluminum; tri-n-octyl aluminum; tri-n-decyl aluminum; tri-n-dodecyl aluminum; tri-n-tetradecyl aluminum; tri-n-hexadecyl aluminum; tri-n-eicosyl aluminum; tri-n-docosanyl aluminum; tri-n-tricosyl aluminum; diethyl n-butyl aluminum; ethyl, n-butyl, n-hexyl aluminum; n-decyl, n-dodecyl, n-tetradecyl aluminum; and the like, and mixtures thereof. A preferred trialkyl aluminum reactant is a mixture of trialkyl compounds generated in a chain growth process, such as that described in U.S. Pat. No. 3,391,219 (Davis et al.), incorporated herein by reference. The displacement reaction described therein results in a peaked production of the more desired olefins. Since the trialkyl aluminum compounds produced by this reference procedure results from ethylene chain growth, the alkyl groups to be displaced will contain an even number of carbon atoms. Triethyl aluminum, tri-n-butyl aluminum, and mixtures of tri-n-alkylaluminum in the effluent from the displacement reaction may be distilled and recycled.

As indicated, the 1-olefin(s) used in the displacement reaction may be any 1-olefin, such as those containing from 2 through 30 carbon atoms. Accordingly, 1-olefins such as ethylene, propylene, 1-butene, 1-hexene, 1-octene, 1-decene, 1-dodecene, 1-tetradecene, 1-hexadecene, 1-octadecene, 1-eicosene, 1-tricontene, vinylidenes, and the like, or mixtures thereof, in all proportions, may be used. The 1-olefin need not be pure, and may contain a variety of non-interfering components, such as paraffins, internal and trisubstituted olefin diluents. In the aspect of the invention wherein an internal olefin or olefins are first isomerized in the reaction mixture, the internal olefin or olefins utilized will be that or those which isomerize to the 1-olefin or 1-olefins mentioned. For chain growth procedures, the displacing olefin will preferably comprise one or more 1-olefins containing from 4 to 30, preferably from 4 to 16 carbon atoms. Most preferably, the olefin employed for chain growth is ethylene. As will be apparent to those of ordinary skill in the art, to achieve any useful result, the displacing 1-olefin will have to be different in nature or carbon distribution from the 1-olefin resulting from the displacement procedure.

If it is desired to replace all or substantially all of the alkyl groups in a trialkyl aluminum compound or compounds, the amount of 1-olefin should be in stoichiometric excess with respect to the amount required to replace the alkyl groups in the trialkyl aluminum. For replacing 1-olefins other than ethylene, the amount of 1-olefin should be at least 200 percent stoichiometric excess with respect to the alkyl groups of the trialkyl aluminum compound or compounds, most preferably 500 percent stoichiometric excess. When ethylene is deployed as the displacing 1-olefin, the amount of ethylene should be in the range of about 10–500 percent stoichiometric excess with respect to the alkyl groups of the trialkyl aluminum compound or compounds, most preferably about 100 percent stoichiometric excess.

Any nickel, cobalt, or mixture of nickel and cobalt, catalyst for the displacement, isomerization/displacement, or chain growth/displacement reactions may be employed. Suitable nickel displacement catalysts are described in the aforementioned U.S. Pat. No. 4,918,254 and U.S. Pat. No. 5,274,153, while suitable cobalt catalysts are described in U.S. Pat. No. 5,191,145, also incorporated herein by reference. The catalysts will be supplied in appropriate amounts, i.e., catalytic amounts, as described in the aforementioned patents.

Conditions for the displacement (displacement conditions), i.e., process conditions for the displacement of an alkyl group from a trialkylaluminum compound or compounds, the isomerization/displacement, and the chain growth/displacement reactions are well known, and per se form no part of the present invention. In general, however, nickel and cobalt catalysts provide the ability to operate at temperatures such as −10° C. to 15° C. Pressures will normally range from about 1 atm. to about 200 atm., preferably from 2 atm. to 40 atm. Proportions of the reactants are described in the aforementioned patents, and may be determined by those of ordinary skill in the art. In general, those of ordinary skill in the art can control the parameters of the general displacement reaction and the specific embodiments. Unless otherwise specified, all percentages of components expressed herein are by weight, based on the total weight of the mixture containing the component or components.

An important requirement of the invention is the timing of the addition of the silver, thallium, or mixture of silver and thallium, catalyst poison. Because the displacement and side reactions proceed concurrently, the catalyst poison must be added, for best results, at a time when the displacement reaction has gone to the desired extent, i.e., to the desired degree of completion, e.g., to completion or at least substantially to completion, but before the side reactions become significant. By "significant" is meant that the amount of undesired by-products formed does not exceed an amount which would render the olefin displaced unsuitable for an intended purpose. In general, the 1-olefin displaced or recovered should contain less than 25 weight percent of side reaction products, most preferably not more than 20 weight percent of side reaction products. The time when the reaction has gone to the desired extent, e.g., at least substantially to completion, is readily determined by a minimal amount of analysis or experimentation. Thus, analysis of the reactant mixture may be conducted on a periodic or continuous basis to determine the concentration of particular components or side products, and the reaction may be terminated by adding a deactivating amount of the silver and/or thallium catalyst poison of the invention. For example, the reaction may be terminated by addition of a deactivating quantity of a solution containing silver, such as a solution containing Ag(I)carboxylate or such as silver (2-ethyl-hexanoate) after a reaction period of from about thirty seconds to an hour. Preferred reaction times for the displacement reaction will range from 2 minutes to 40 minutes, most preferably from 5 to 30 minutes. As a practical matter, the silver and/or thallium catalyst poison may be added when it is determined by analysis or experience that the displacement reaction as shown in Equation I has approached or reached chemical or thermodynamic equilibrium.

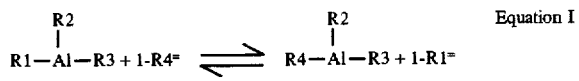

Equation I

In Equation I, R1, R2, and R3 are the alkyl groups attached to the aluminum and may all be the same, may all be different, or only two may be the same. R1 is the desired alkyl which is to be displaced from the aluminum and subsequently recovered as a 1-olefin. Also in Equation I, 1-R4⁼ represents the displacing 1-olefin and 1-R1⁼ represents the displaced 1-olefin. In the presence of catalyst (usually nickel and/or cobalt), an appropriate stoichiometric excess of 1-R4⁼ will displace R1 from the aluminum thereby forming the desired 1-R1⁼.

As indicated, the silver and/or thallium containing catalyst poison is added to the displacement reaction system or solution in an amount that will deactivate the nickel and/or cobalt catalyst. That is, a deactivating amount of the catalyst poison will be supplied, i.e., an amount or concentration sufficient to inhibit or at least substantially prevent the catalytic action of the nickel and/or cobalt catalyst, and this amount may readily be determined by those of ordinary skill in the art. Other catalyst poisons may be employed with the Ag and/or TI catalyst poisons of the invention, preferably in minor amount, provided the effect of the Ag and/or TI catalyst poisons of the invention is not significantly reduced and the advantages accruing from the invention are not significantly diminished. The catalyst poison, Ag and/or TI, should be used in at least a one to two molar excess to the nickel and/or cobalt to give effective deactivation of the Ni and/or Co catalyst. The catalyst poisons of this invention may be supplied in any suitable means. In one embodiment, the reaction solution is contacted with the poisons which are present on a solid support.

Preferably, the catalyst poisons of the invention will be supplied to the reaction mixture as solutions containing Ag and/or TI, usually containing from about 0.5 weight percent to about 20 weight percent of the poison(s), providing an excess over the Ni and/or Co mentioned. For simplicity, the terms "silver" and "thallium" are to be understood, in the claims appended hereinafter, unless inconsistent with the clearly intended meaning, as covering the solid elemental, ionic or chemically bound and complexed forms of the respective metals. Although the metal or metals may be added directly, e.g., as finely divided solids, the poisons are preferably added as solutions containing the metals, most preferably as solutions of compounds or complexes which have deactivating capability. Suitable silver compounds include silver carboxylates, silver acetylacetonate, silver sulfonates, silver neodecanoates, and the like and suitable silver complexes include tetranitrile Ag$^{+1}$ complexes. Suitable thallium compounds include thallium carboxylates, thallium alkoxides, and the like while suitable thallium complexes include Tl$^{+1}$ dithiocarbamates.

After the catalyst poison of the invention has been added, any trialkyl aluminum product can be recovered by conventional methods, such as by distillation. Should the catalyst poison metals precipitate in solution, they may easily be removed by adding filtration aids, such as alumina powder or carbon powder.

EXAMPLES

The ability of the catalyst poisons of the invention to deactivate displacement catalyst(s) is supported by the following experiments. Experiment I represents a base case illustrating the reactions occurring with a Ni catalyst.

Experiment I

Under nitrogen atmosphere, 600 microliters of Ni(II) 2-ethylhexanoate in heptane solution (1.266 milligrams Ni(II)/cc solution) were added to 12.9 grams of 1-hexene and 2.62 grams of hydride-free tri-n-propyl aluminum at 45° C. over approximately 2 seconds. The reaction mixture cooled to 30° C. in 2 minutes because of the liberation of propylene gas. At this juncture, the reaction mixture was heated slowly to 50° C. (66 minutes). Samples were then taken by syringe in 0.5 cc aliquots from the reaction mixture and hydrolyzed in 2N HCl solution with 10 cc of heptane diluent present. The diluent served to absorb most of the propylene and propane present in the liquid and diluted the sample for gas chromatographic analysis. The 2N HCl was added to hydrolyze any aluminum alkyl species present to water-soluble aluminum salts and alkanes which correspond to the alkyl groups present (e.g., tri-n-propyl aluminum produces propane, tri-n-hexyl aluminum gives hexane).

The results were analyzed by gas chromatographic procedure. The gas chromatographic procedure utilized a 30° C. isothermal program and a polar phase capillary column to get olefin isomer separation for the flame ionization detector to give area percentages of hydrocarbon. The results are reported in Table I below wherein the percent area beneath each heading is substantially equivalent to the weight percent of the species denominated.

TABLE I

Experiment I Data
GAS CHROMATOGRAPHY AREA PERCENTAGES

| Sample Time (in minutes) | Temp. °C. | C3 Groups | 1-hexene | internal hexenes | hexane |
|---|---|---|---|---|---|
| 0 | 45 | 11.52 | 86.2 | 0 | 0.8 |
| 2.25 | 30 | 2.29 | 63.8 | 0.54 | 31.9 |
| 66 | 50 | 0.24 | 26.6 | 34.18 | 37.8 |

Although not shown, the gas chromatographic results also indicate about 1.5 weight percent of 2-ethyl-butene present in all samples. The C3 groups represent a sum of propylene and propane present in the sample, but mostly propane since the propylene was vented to maintain atmospheric pressure in the reactor.

The experiment demonstrates that nickel catalyzes displacement, as evidenced by the increase in hexane after 2.25 minutes. Unfortunately, isomerization also occurs over a period of time, as shown by the increase in internal hexenes at the expense of the 1-hexene after 66 minutes.

Experiment II

Sixty microliters of heptane containing 0.0056 grams of Ni(II), supplied as Ni(II)2-ethyl-hexanoate, were added, under nitrogen atmosphere, to a mixture of 2.4 grams of hydride-free tri-n-propyl aluminum and 5.6 grams of 1-hexene over a period of about 10 seconds, the initial temperature of the mixture being 20.9° C. After 2 minutes, 100 microliters of solution of Ag(I) neododeconate in heptane (0.007 g Ag(I)/cc of heptane), at a temperature of 25.4° C., were added to the reaction mixture over a period of about 10 seconds. Upon completion of the Ag(I) addition, 10 grams of 1-octene were added immediately to the reaction mixture. To insure that enough Ag(I) was present to suppress the isomerization reaction, an additional 100 microliters of the aforementioned Ag(I) neododeconate solution were added to the reaction mixture.

After 5 minutes, a sample was removed from the reaction mixture and hydrolyzed with cold dilute HCl (2N), and analyzed as hereinafter indicated. The reaction mixture was then heated to 60° C. and stirred for 10 minutes at 56.60° C. to 60° C. At this point, a second sample was taken and hydrolyzed as indicated.

The reaction mass was then heated to 121.6° C. and refluxed for 30 minutes at 121.4° C. to 122.8° C. Third and fourth samples were removed, respectively, after 10 and 30 minutes of refluxing, and each hydrolyzed as indicated. The reaction mixture was black in color, but no noticeable agglomeration of particles was observed. The samples were analyzed by standard gas chromatography procedure. The results are reported in Table II below, wherein, as indicated, percent area beneath each heading is substantially equivalent to the weight percent of the species denominated.

TABLE II

Experiment II Data
GAS CHROMATOGRAPHY AREA PERCENTAGES

| Sample Number | 1-hexene | internal hexenes | hexane (from $C_6$-Al<) | 1-octene | internal octenes | octane (from $C_8$-Al<) |
|---|---|---|---|---|---|---|
| 1 | 32.76 | 0.31 | 8.27 | 38.75 | 0.15 | 11.80 |

TABLE II-continued

Experiment II Data
GAS CHROMATOGRAPHY AREA PERCENTAGES

| Sample Number | 1-hexene | internal hexenes | hexane (from $C_6$-Al<) | 1-octene | internal octenes | octane (from $C_8$-Al<) |
|---|---|---|---|---|---|---|
| 2 | 32.36 | 0.21 | 0.62 | 34.80 | 0.25 | 15.83 |
| 3 | 3.67 | 0.03 | 14.87 | 45.50 | 0.45 | 29.86 |
| 4 | 3.57 | 0.02 | 13.46 | 44.33 | 0.48 | 31.69 |

The experiment demonstrates a significant inhibition of internal isomerization, i.e., reduced presence of internal hexenes and internal octenes. Area percents do not add up to 100 percent since propane and propylene are not included in the table.

Experiment III

Three grams of tri-n-butyl aluminum, 15 grams of 1-octene, and 0.12 grams of dry, fine-activated carbon powder were charged to a flask. Under nitrogen atmosphere, the mixture was heated to and stirred at 62° C. to 70° C. for ten minutes, and then cooled to 20.6° C. Sixty microliters of heptane containing 0.0056 grams Ni(II), supplied as Ni(II) 2-ethyl-hexanoate, were added to the mixture over a period of about 10 seconds. After 2 minutes, 80 microliters of solution of Ag(I) neododeconate in heptane (0.007 g Ag(I) /cc heptane) were added over a period of about 10 seconds.

After 5 minutes, a first sample was taken, hydrolyzed with cold dilute HCl (2N), and analyzed as hereinafter indicated. The reaction mixture was then heated to 60° C. and stirred for 10 minutes at 60° C. to 65° C., after which a second sample was taken. The mixture was then heated and stirred at 120° C. to 125° C. for 10 minutes, after which a third sample was taken. On cooling, agglomerated black powder was filtered from the reaction mixture, leaving a very light brown filtrate. The results of the silver addition are shown in the following table.

TABLE III

Experiment III Data
GAS CHROMATOGRAPHY AREA PERCENTAGES

| Sample Number | 1-butene | 2-butene | butane (from $C_4$-Al<) | 1-octene | internal octenes | octane (from $C_8$-Al<) |
|---|---|---|---|---|---|---|
| 1 | 11.26 | (trace) | 11.13 | 55.37 | 0.66 | 21.06 |
| 2 | 8.91 | 0.04 | 7.10 | 51.20 | 0.50 | 31.17 |
| 3 | 0.15 |  | 6.02 | 55.64 | 0.67 | 36.08 |

The addition of silver to the reaction mixture in the manner of the invention suppresses the isomerization to 2-butene and internal octenes.

Experiment IV

Sixty microliters of heptane containing 0.0056 grams Ni(II), supplied as Ni(II) 2-ethyl-hexanoate, are added to a mixture of 2.4 grams of hydride-free tri-n-propyl aluminum and 5.6 grams of 1-hexene in a flask over a period of about 10 seconds, the temperature being about 22° C. After 2 minutes, 80 microliters of a solution of Tl(I)ethyl-hexanoate in heptane (about 0.029 g Tl(l)/cc), prepared by dissolving 0.5 grams of Tl(I)ethyl-hexanoate in 10 cc of heptane and a few drops of 2-ethyl-hexanoic acid), were added to the reaction mixture over a period of about 10 seconds. Ten grams of 1-octene were then added. A first sample was taken and hydrolyzed, in the manner described previously, five minutes after the 1-octene addition. The reaction mixture was heated to 60° C. and stirred at about 60° C. for ten minutes, after which a second sample was taken. The reaction mixture was heated up to and refluxed at 120° C. for 30 minutes before the last sample was taken. Results of gas chromatography analysis are shown in Table IV below.

TABLE IV

Experiment IV Data
GAS CHROMATOGRAPHY AREA PERCENTAGES

| Sample Number | 1-hexene | internal hexenes | hexane (from $C_6$-Al<) | 1-octene | internal octenes | octane (from $C_8$-Al<) |
|---|---|---|---|---|---|---|
| 1 | 31.91 | 0.25 | 8.46 | 46.39 | 0.37 | 1.56 |
| 2 | 33.84 | 0.31 | 9.14 | 42.59 | 0.34 | 4.59 |
| 3 | 4.68 | 0.02 | 14.02 | 47.15 | 0.51 | 22.72 |

The Tl(I) addition results in a mixture having little internal hexene and little internal octene.

Specific compositions and procedures described are intended to be only illustrative of the invention disclosed by this specification. Obvious variations on these compositions or methods will be readily apparent to a person of ordinary skill in the art based on the teachings of this specification and are therefore intended to be included as part of the invention disclosed herein.

What is claimed is:

1. A process for deactivating a displacement catalyst selected from the group consisting of nickel, cobalt and mixtures thereof during a reaction wherein an alkyl group is displaced from a trialkyl aluminum compound in a reaction mixture containing said catalyst comprising adding to the reaction mixture a deactivating amount of a catalyst poison containing a member selected from the group consisting of silver, thallium, and mixtures thereof after the displacement has proceeded to the desired extent.

2. The process of claim 1 wherein the catalyst poison is added before undesired isomerization of any 1-olefin displaced from the trialkyl aluminum compound has occurred.

3. The process of claim 1 wherein the catalyst poison is added when reaction has proceeded to about thermodynamic equilibrium.

4. The process of claim 1 wherein the catalyst poison is silver.

5. The process of claim 1 wherein any precipitates formed as a result of the presence of catalyst killer are removed by filtration including optional employment of a filtration aid selected from the group consisting of alumina powder and carbon powder.

6. A process for the displacement of at least one alkyl group from a first trialkyl aluminum compound in which the three alkyl groups are not necessarily the same, comprising, contacting the first trialkyl aluminum compound with 1-olefin containing a different distribution of carbon atoms than the alkyl groups in the first trialkyl aluminum compound, in the presence of a catalyst selected from the group consisting of nickel, cobalt, and mixtures thereof under displacement conditions, wherein said 1-olefin displaces at least some of the alkyl groups in the first trialkyl aluminum to form a second trialkyl aluminum compound, and adding to the reaction mixture a deactivating amount of a catalyst poison selected from the group consisting of silver, thallium, and mixtures thereof wherein the catalyst poison is added after the displacement has proceeded to the desired extent.

7. The process of claim 6 wherein the catalyst poison is added before significant isomerization of any 1-olefin displaced from the trialkyl aluminum compound has occurred.

8. The process of claim 6 wherein the catalyst poison is added when reaction has proceeded to about thermodynamic equilibrium.

9. The process of claim 6 wherein the catalyst poison is silver.

10. The process of claim 6 wherein any precipitates formed as a result of the presence of catalyst killer are removed by filtration including optional employment of a filtration aid selected from the group consisting of alumina powder and carbon powder.

11. The process of claim 6 wherein the first trialkyl aluminum compound is a mixture of trialkyl aluminum compounds and wherein the second trialkyl aluminum compound is a mixture of trialkyl aluminum compounds.

12. The process of claim 6 wherein the 1-olefin is a mixture of 1-olefins.

13. A process comprising reacting ethylene with a first trialkyl aluminum compound having three starting alkyl groups under chain growth conditions to form a reaction mixture comprising a second trialkyl aluminum compound having at least one longer carbon chain alkyl group, displacing at least one longer chain alkyl group with 1-olefin under displacement conditions in the presence of a catalyst selected from the group consisting of nickel, cobalt, and mixtures thereof to form 1-olefin of longer carbon chain length than the starting alkyl group, adding a deactivating amount of a catalyst poison selected from the group consisting of silver, thallium, and mixtures thereof to the reaction mixture after the displacement has proceeded to the desired extent, and removing the 1-olefin formed by the displaced longer chain alkyl groups from the reaction zone.

14. The process of claim 13 wherein the catalyst poison is added before significant isomerization of the longer carbon chain 1-olefins displaced from the trialkyl aluminum compound has occurred.

15. The process of claim 13 wherein the catalyst poison is added when reaction has proceeded to about thermodynamic equilibrium.

16. The process of claim 13 wherein the catalyst poison is silver.

17. The process of claim 13 wherein any precipitates formed as a result of the presence of catalyst killer are removed by filtration including optional employment of a filtration aid selected from the group consisting of alumina powder and carbon powder.

* * * * *

UNITED STATES PATENT AND TRADEMARK OFFICE
CERTIFICATE OF CORRECTION

PATENT NO.: 5,780,697

DATED: July 14, 1998

INVENTOR(S): Ronny Wen-Long Lin, Richard Andrew Holub, Richard Neil Hollenshead

It is certified that error appears in the above-identified patent and that said Letters Patent is hereby corrected as shown below:

| Col. | Line | |
|------|------|---|
| 5 | 54-55 | reads "the Ag and/or TI catalyst poisons" should read --the Ag and/or Tl catalyst poisons-- |
| 5 | 56-57 | reads "the effect of the Ag and/or TI catalyst poisons" should read --the effect of the Ag and/or Tl catalyst poisons-- |
| 5 | 59 | reads "The catalyst poison, Ag and/or TI" should read --The catalyst poisons, Ag and/or Tl-- |
| 5-6 | 67-1 | reads "solutions containing Ag and/or TI" should read --solutions containing Ag and/or Tl -- |
| 8 | 64 | reads "a solution of TI(I)ethyl-hexanoate" should read --a solution of Tl(I)ethyl-hexanoate-- |
| 8 | 65 | reads "in heptane (about 0.029 g TI(I)/cc) should read --in heptane (about 0.029 g Tl(I)/cc) |

UNITED STATES PATENT AND TRADEMARK OFFICE
CERTIFICATE OF CORRECTION

PATENT NO.: 5,780,697
DATED: July 14, 1998
INVENTOR(S): Ronny Wen-Long Lin, Richard Andrew Holub, Richard Neil Hollenshead It is certified that error appears in the above-identified patent and that said Letters Patent is hereby corrected as shown below:

| Col. | Line |  |
|------|------|---|
| 8 | 66 | reads "0.5 grams of TI(I)ethyl-hexanoate" should read --0.5 grams of Tl(I)ethyl-hexanoate-- |
| 9 | 22 | reads "The TI(I) addition results in a mixture" should read --The Tl(I) addition results in a mixture-- |

Signed and Sealed this

Twenty-ninth Day of December, 1998

Attest:

BRUCE LEHMAN

*Attesting Officer*     Commissioner of Patents and Trademarks